United States Patent
Bado et al.

(10) Patent No.: US 8,743,353 B2
(45) Date of Patent: Jun. 3, 2014

(54) DEVICE AND METHOD FOR DETECTING BLOOD OR BLOOD CONSTITUENTS IN THE LIQUID SYSTEM OF A DEVICE FOR EXTRACORPOREAL BLOOD TREATMENT

(75) Inventors: Itka Bado, Frankfurt (DE); Peter Scheunert, Friedrichsdorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 69 days.

(21) Appl. No.: 13/388,603

(22) PCT Filed: Jul. 31, 2010

(86) PCT No.: PCT/EP2010/004697
§ 371 (c)(1),
(2), (4) Date: Mar. 19, 2012

(87) PCT Pub. No.: WO2011/015321
PCT Pub. Date: Feb. 10, 2011

(65) Prior Publication Data
US 2012/0170020 A1 Jul. 5, 2012

(30) Foreign Application Priority Data

Aug. 4, 2009 (DE) .................. 10 2009 036 044

(51) Int. Cl.
*G01N 33/48* (2006.01)
*G01N 33/49* (2006.01)
*G01N 21/25* (2006.01)

(52) U.S. Cl.
CPC .............. *G01N 33/49* (2013.01); *G01N 21/251* (2013.01)
USPC .............................................. 356/39; 356/40

(58) Field of Classification Search
CPC ............................. G01N 33/38; G01N 21/251
USPC ....................................................... 356/39–42
See application file for complete search history.

(56) References Cited

U.S. PATENT DOCUMENTS 4,166,961 A * 9/1979 Dam et al. ................. 250/573
4,181,610 A * 1/1980 Shintani et al. ................. 210/85
(Continued)

FOREIGN PATENT DOCUMENTS

DE 20 2004 003335 U1 6/2004
DE 10 2006 029 899 A1 1/2008
JP 62000838 A 1/1987

OTHER PUBLICATIONS

International Search Report from PCT/EP2010/004697, mailed on Nov. 25, 2010.

*Primary Examiner* — Michael P Stafira
(74) *Attorney, Agent, or Firm* — Kenyon and Kenyon LLP

(57) ABSTRACT

The present invention relates to a device and a method for detecting blood or blood constituents in the liquid system of a device for extracorporeal blood treatment, comprising a dialysis device or filter divided by a semipermeable membrane into a first chamber and a second chamber, wherein the first chamber is part of the extracorporeal blood circulation system and the second chamber part of the liquid system of the extracorporeal blood treatment device. The device according to the present invention for detecting blood or blood constituents in the liquid system of an extracorporeal blood treatment device is designed as a unit for differentiating between the entry of blood into the liquid system due to a defect of the dialysis device or filter, for example a rupture of the semipermeable membrane of the dialysis device or filter, or the entry of hemoglobin into the liquid system due to hemolysis, wherein a differentiation is made between a defect of the dialysis device or filter or hemolysis based on the change in intensity of at least the blue fraction of the light exiting from the liquid.

20 Claims, 5 Drawing Sheets

(56) References Cited

U.S. PATENT DOCUMENTS

| | | |
|---|---|---|
| 6,348,156 B1 | 2/2002 | Vishnoi et al. |
| 8,054,452 B2 | 11/2011 | Bado et al. |
| 2003/0210390 A1 | 11/2003 | O'Mahony et al. |
| 2005/0045540 A1 | 3/2005 | Connell et al. |
| 2005/0094127 A1* | 5/2005 | O'mahony et al. ............. 356/39 |
| 2007/0259436 A1 | 11/2007 | Tarasev |
| 2009/0257061 A1* | 10/2009 | Wihlborg ...................... 356/433 |
| 2009/0279071 A1 | 11/2009 | Bado et al. |
| 2010/0110416 A1* | 5/2010 | Barrett et al. .................. 356/40 |

* cited by examiner

DEVICE AND METHOD FOR DETECTING BLOOD OR BLOOD CONSTITUENTS IN THE LIQUID SYSTEM OF A DEVICE FOR EXTRACORPOREAL BLOOD TREATMENT

CROSS REFERENCE TO RELATED APPLICATIONS

This is a 371 national phase application of PCT/EP2010/004697 filed Jul. 31, 2010, claiming priority to German Patent Application No. 10 2009 036 044.1 filed Aug. 4, 2009.

FIELD OF INVENTION

The present invention relates to a device and a method for the detection of blood or blood constituents in the fluid system of an apparatus for extracorporeal blood treatment, which comprises a dialyzer or filter divided by a semipermeable membrane into a first chamber and a second chamber, wherein the first chamber is part of the extracorporeal blood circuit and the second chamber is part of the fluid system of the extracorporeal blood treatment apparatus.

BACKGROUND OF THE INVENTION

Various methods for extracorporeal blood treatment are known. In hemodialysis (HD), the patient's blood is cleaned in an extracorporeal blood circuit which comprises a dialyzer. The dialyzer comprises a blood chamber and a dialyzing fluid chamber, which are separated by a semipermeable membrane. Whereas dialyzing fluid flows through the dialyzing fluid chamber in hemodialysis (HD), substances being transported through the membrane on account of the diffusion between the dialyzing fluid and the blood, dialyzing fluid does not flow through the dialyzing fluid chamber of the dialyzer in the case of hemofiltration (HF). In the case of hemofiltration (HF), certain substances are effectively removed through the membrane of the filter by convection. Hemodiafiltration (HDF) is a combination of both methods.

In the performance of an extracorporeal blood treatment, there is basically the risk of a rupture of the semipermeable membrane of the dialyzer or filter. The casting compound of the dialyzer or filter can also become detached. In the case of a defect of the dialyzer or filter, blood passes out of the extracorporeal blood circuit into the fluid system of the blood treatment apparatus. With the known blood treatment apparatuses, therefore, the entry of blood into the fluid system due to a defect of the dialyzer or filter is monitored. The detection of blood in the fluid system takes place according to the prior art with an optical measuring method, wherein the reduction in the intensity of light passing through the dialyzing fluid is evaluated. When blood enters into the dialyzing fluid, the intensity of the light exiting from the dialyzing fluid changes, the change in intensity being dependent on the wavelength of the light. An entry of blood into the fluid system can be reliably detected with the known methods.

Apart from the entry of blood into the fluid system due to a defect of the dialyzer or filter, for example due to a membrane rupture or a casting compound detachment, free hemoglobin or its constituents can also get into the dialyzing fluid in an extracorporeal blood treatment due to a hemolysis. Hemolysis denotes the dissolution (destruction) of the erythrocytes (red blood corpuscles) of the blood. The erythrocytes substantially consist of the oxygen-binding protein hemoglobin, which endows the erythrocytes and therefore the blood with the red color. When hemolysis occurs, hemoglobin is released.

In an extracorporeal blood treatment, a hemolysis can occur for example due to a mechanical strain on the blood due to shear flows. Such shear flows occur, amongst other things, when a blood-carrying hose line of the hose line system of the blood treatment apparatus is kinked. A hemolysis can however also be caused systemically due to the patient.

In extracorporeal blood treatment, hemoglobin can also defuse from the blood side of the dialyzer through the semipermeable membrane onto the dialysate side. The hemoglobin can therefore be detected in the blood with the optical measuring methods known according to the prior art.

A drawback is that, with the known optical measuring methods, it is not possible to distinguish between the entry of blood due to a defect of the dialyzer or filter or the entry of hemoglobin as a blood constituent due to a hemolysis. Different measures have to be taken, however, in the case of a defect of the dialyzer or filter or in the case of a hemolysis. Thus, for example, the dialyzer must be replaced in the case of a membrane rupture, whereas in the case of a hemolysis the user must be prompted to take suitable countermeasures, for example to replace the hose system or at least to free it from the kinked point.

The monitoring devices generally used in extracorporeal blood treatment to detect an entry of blood or a hemolysis are based on the spectroscopic evaluation of the red and green component of light. In this wavelength region, however, it is not possible to distinguish between blood and hemoglobin.

US 2007/0259436 A1 describes a method for detecting hemoglobin in the blood, wherein light with a wavelength of 390 to 460 nm passes through a sample. The change in the light intensity is determined for two or more wavelengths.

A method for detecting a hemolysis, wherein the reduction in the intensity of the blue component of light is taken into account, is also known from JP 62000838A.

SUMMARY OF THE INVENTION

The problem underlying the present invention is to make available a device which, when blood or blood constituents enter into the fluid system of the extracorporeal blood treatment apparatus, permits a decision to be made for the initiation of targeted countermeasures. Moreover, a problem of the present invention is to provide a method which enables a decision to be made for the initiation of targeted countermeasures when blood or blood constituents enter into the fluid system of the blood treatment apparatus.

The device according to the present invention for detecting blood or blood constituents in the fluid system of an extracorporeal blood treatment apparatus is designed as a device for distinguishing between the entry of blood into the fluid system due to a defect in the dialyzer or filter, for example a rupture of the semipermeable membrane of the dialyzer or filter, and the entry of hemoglobin into the fluid system due to a hemolysis, wherein a defect in the dialyzer or filter or a hemolysis is ascertained on the basis of the change in the intensity of light that passes through the fluid present in the fluid system.

It has been shown that the quotient of the intensity of the red or green component of the light exiting from the fluid and the intensity of the blue component of the exiting light increases when non-hemolysised blood gets into the dialyzing fluid. The quotient of the intensity of the red component and green component of the light exiting from the fluid also increases when non-hemolysised blood gets into the dialyzing fluid. When hemolysised blood gets into the dialyzing fluid, the quotient of the intensity of the red component and blue component or the quotient of the intensity of the red component and green component increases. The quotient of the green component and blue component, on the other hand, does not change or does not change significantly with the entry of hemolysised blood.

A distinction between the entry of hemolysised and non-hemolysised blood can thus be made by the fact that the ratio of the red component and the blue component of the light exiting from the fluid is evaluated. It has been shown that the quotient of the red component and blue component increases more markedly with the entry of non-hemolysised blood than with the entry of hemolysised blood. A distinction between the entry of hemolysised and non-hemolysised blood can also be made by the fact that the ratio of the green component and the blue component of the light exiting from the fluid is evaluated, since a significant increase in the quotient appears only in the case of the entry of non-hemolysised blood.

A preferred embodiment of the present invention makes provision for a distinction to be made between the entry of blood into the fluid system due to a defect in the dialyzer or filter and the entry of hemoglobin into the fluid system due to a hemolysis on the basis of the change in the intensity of at least the blue component of the light exiting from the fluid. Apart from the blue component, however, other components of the light, for example the red component and/or the green component, can also be evaluated. It has been shown that the evaluation of the blue component permits a reliable distinction to be made between blood and the blood constituent hemoglobin in the dialyzing fluid.

A further particularly preferred embodiment provides for the evaluation both of the blue component and the red component. The intensity of the blue component of the light exiting from the fluid on the one hand and the intensity of the red component of the light exiting from the fluid on the other hand are determined. The intensity of the red component is compared with the intensity of the blue component. Since the change in the light intensity both of the blue component and the red component are evaluated and related to one another, it is possible to distinguish reliably between blood and hemoglobin. The intensity of the light entering into the fluid does not play any role for the device according to the present invention and the method according to the present invention, since two different color components are put into a ratio. The device according to the present invention and the method according to the present invention are therefore insensitive to fluctuations in the intensity of the light.

In a preferred embodiment, the quotient of the intensity of the red light and the intensity of the blue light is compared with a preset threshold value and/or the quotient of the intensity of the green light and the intensity of the blue light is compared with a preset threshold value. It is concluded that there is an entry of hemoglobin due to a hemolysis when the quotient is smaller than or equal to the preset threshold value. If, on the other hand, the quotient is greater than the preset threshold value, it is concluded that there is an entry of blood, for example due to a rupture of the membrane. Just one single value can be preselected as the threshold value. It is however also possible to preselect a number of individual values for individual enquiries as the threshold value.

A particularly preferred embodiment first provides for the calculation of the quotient of the red component and the green component of the light exiting from the fluid in order to detect the entry of hemolysised blood or non-hemolysised blood into the dialyzing fluid, without however being able to distinguish between the entry of hemolysised blood or non-hemolysised blood. Only when hemolysised blood or non-hemolysised blood is detected is the quotient of the red and blue component and/or of the green and blue component determined in order to distinguish between a defect in the dialyzer or filter or a hemolysis.

In a preferred embodiment, it is not only the intensity of the light exiting from the fluid that is monitored, but also the intensity of the light entering into the fluid. The monitoring of the intensity of the light entering into the fluid permits the detection of an abnormal occurrence. For example, by comparing the measured intensity of the entering light with a preset threshold value, it is possible to detect whether the means for transmitting the light, for example an LED, are defective. This is especially of interest when light exiting from the fluid is no longer received. This is because the reason for this may be that, instead of dialyzing fluid, blood is present in the fluid system, which represents a massive disruption, or merely that the light source is defective.

It is however also possible to provide a control or regulation with the measured intensity of the light entering into the fluid, in order to keep constant the light intensity of the light source independently of the ambient conditions, particularly the temperature.

The device according to the present invention comprises means for emitting light which enters into the fluid present in the fluid system and means for receiving light which exits from the fluid present in the fluid system. Moreover, the device comprises an evaluation unit for evaluating the intensity of the light entering into the fluid and exiting from the fluid. In a preferred embodiment, means are also provided for receiving light which enters into the fluid present in the fluid system.

In a preferred embodiment, the means for emitting light are a light source which emits white light, for example a white light-emitting LED or a white light-emitting RGB-LED, whilst the means for receiving light are a light sensor which receives different color components of the light. This preferred embodiment has the advantage that the measuring apparatus has a more straightforward structure than a measuring apparatus in which a plurality of light sources are provided, for example a blue, red and green light source, and a plurality of light sensors are provided which, for example, receive blue, red and green light. Moreover, the use of one light source which emits unspecific light (white light) proves to be advantageous, since the measurement result can be influenced less by shifts in the spectrum of the light that is emitted by individual light sources with a narrow wavelength band.

A further particularly preferred embodiment makes provision for an adaptation of the preset threshold value or the preset threshold values to the patient. This makes it possible, even with patients suffering from a systemic hemolysis, to distinguish between the entry of blood or hemoglobin into the fluid system. In the case of an illness-induced higher component of hemoglobin in the blood (systemic hemolysis), the preset threshold value can be suitably adapted, so that it is not concluded, solely on account of the raised component of hemoglobin in the blood due to a systemic hemolysis, that there is an entry of hemoglobin into the dialyzing fluid which can be traced back to damage to the blood, due for example to a kinked blood-conveying hose line. For example, a set of adapted threshold values can be ascertained and preselected on the basis of the patient data.

The adaptation of the preset threshold value or threshold values preferably takes place on the basis of patient-specific data which are preferably inputted on an input unit. It is however also possible for the preset threshold value to be determined as a function of patient-specific data which have been obtained on the basis of a reference measurement. For example, it is possible, before the start or at the start or during the blood treatment, to provide a reference measurement at a time at which a hemolysis is not assumed, for example due to the kinking of a hose line. Deviations from this threshold value then permit the conclusion to be drawn that there is an entry of hemoglobin due to damage to the blood.

If the entry of blood and/or hemoglobin is ascertained, an optical and/or acoustic and/or tactile signal can be emitted in order to initiate suitable countermeasures. For example, the blood treatment can be immediately interrupted in the event of entry of blood. It is also possible for a control signal to be generated for an intervention into the machine control in order to initiate countermeasures automatically.

The result of the monitoring is preferably displayed on a display screen, which may be a so-called touchscreen. Apart from the nature of the occurring complications, i.e. membrane rupture or hemolysis, the recommended countermeasures can be displayed on the monitor, for example by a suitable text and/or suitable symbols. For example, a prompt can be given for the exchange of the hose line system or the dialyzer.

BRIEF DESCRIPTION OF THE DRAWINGS

Examples of embodiment of the present invention are explained in greater detail below by reference to the drawings.

In the figures.

DETAILED DESCRIPTION OF THE DRAWINGS

Figure 1:
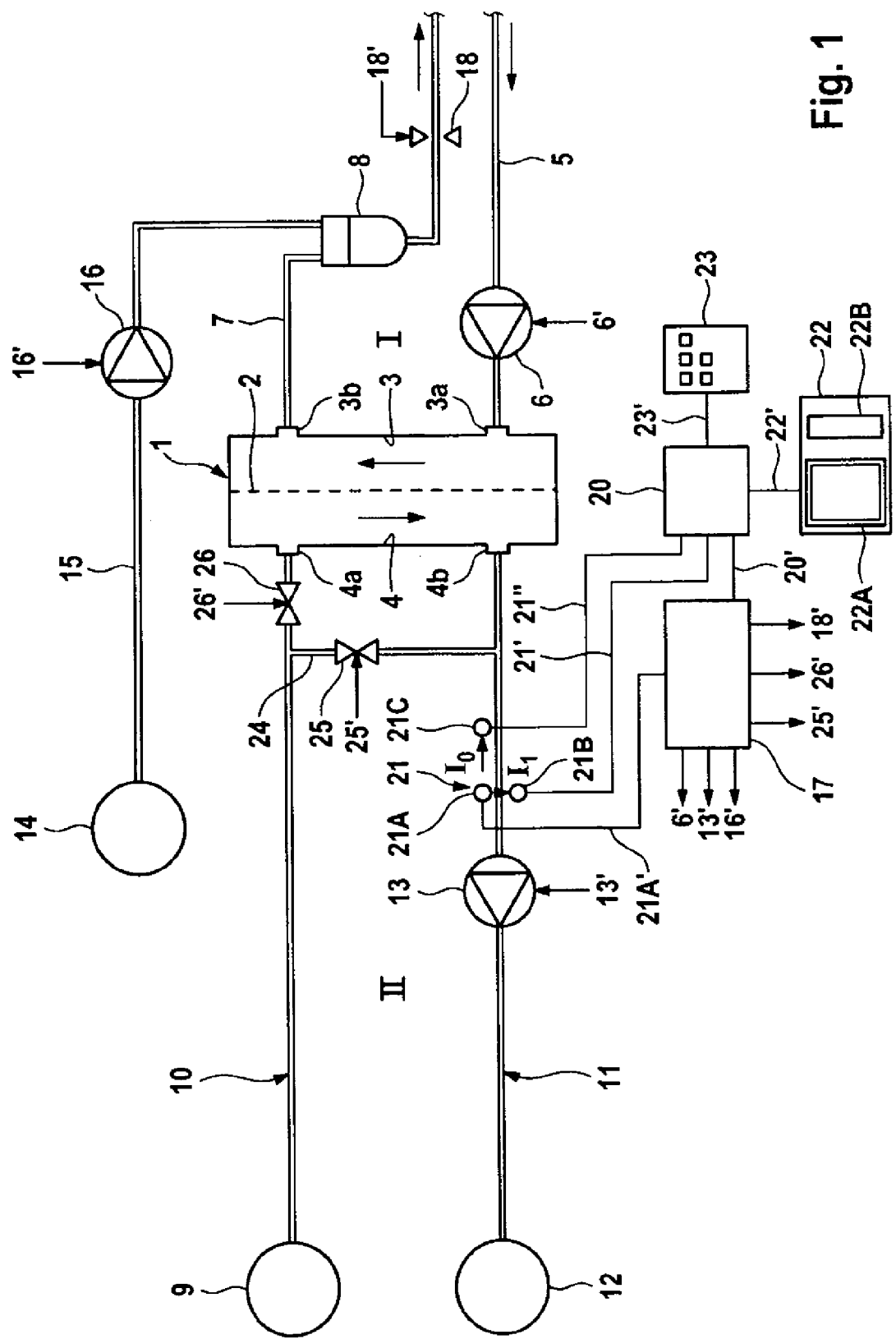
FIG. 1 shows an extracorporeal blood treatment apparatus together with a device for the detection of blood or blood constituents in the fluid system of the blood treatment apparatus in a very simplified schematic representation.

FIG. 1 shows, in a very simplified schematic representation, an example of embodiment of the components of an extracorporeal blood treatment apparatus relevant to the present invention, the treatment apparatus being able to be operated as a hemodialysis apparatus and/or a hemofiltration apparatus. The extracorporeal blood treatment apparatus is therefore also referred to below as a hemodiafiltration apparatus.

The hemodiafiltration apparatus comprises a dialyzer or filter 1, which are divided by a semipermeable membrane 2 into a blood chamber 3 and a dialyzing fluid chamber 4. Inlet 3a of the blood chamber is connected to one end of an arterial blood supply line 5, into which a blood pump 6 is incorporated, whilst outlet 3b of the blood chamber is connected to one end of a venous blood return line 7, into which a drip chamber 8 is incorporated. Located at the other ends of arterial and venous blood line 5, 7 are the arterial and venous cannulas (not shown) for connection to the patient. This part of the fluid system represents extracorporeal blood circuit I of the hemodiafiltration apparatus. Blood lines 5, 7 are hose lines of a hose line system intended for one-time use, which is inserted into the blood treatment apparatus.

Fluid system II of the hemodiafiltration apparatus comprises a device 9 for making available fresh dialyzing fluid, which is connected via a dialyzing fluid supply line 10 to inlet 4a of dialyzing fluid chamber 4 of dialyzer 1 or filter. Leading away from outlet 4b of dialyzing fluid chamber 4 of dialyzer 1 or filter is a dialyzing fluid return line 11, which leads to a drain 12. A dialyzing fluid pump 13, which is incorporated into the dialyzing fluid return line, is used to convey the dialyzing fluid.

Furthermore, the hemodiafiltration apparatus comprises a substituate source 14, from which a substituate line 15, into which a substituate pump 16 is incorporated, leads to venous drip chamber 8. A predetermined amount of substitution fluid can be fed from the substituate source to extracorporeal blood circuit I by means of the substituate pump when fluid is removed from extracorporeal blood circuit I via dialyzer 1.

The hemodiafiltration apparatus further comprises a central control and computing unit 17, which is connected via control lines 6', 13', 16' to blood pump 6, dialyzing fluid pump 13 and substituate pump 16. Control and computing unit 17 sends control commands to the individual components and receives data from the components concerning their operational states.

The device according to the present invention for the detection of blood or blood constituents in the fluid system of the extracorporeal blood treatment apparatus is described below. The device according to the present invention for the detection of blood or blood constituents can form an independent unit or be a component of the blood treatment apparatus. In the present example of embodiment, the device according to the present invention is a component of the blood treatment apparatus.

With the exception of the measuring arrangement, the device according to the present invention can make use of the parts which are already present in the known extracorporeal blood treatment apparatuses. For example, the device according to the present invention can make use of the central control and computing unit of the blood treatment apparatus in order to evaluate the acquired measurement data. The device according to the present invention can also use the display unit and the input unit of the blood treatment apparatus. A separate evaluation unit can however also be provided for the device according to the present invention. A separate display unit or input unit can also be present.

The device for the detection of blood or hemoglobin comprises a light source 21A, for example an LED, and a light sensor 21B, which are arranged opposite one another. Light source 21A and light sensor 21B form a measuring arrangement 21 for measuring the change in the intensity of light exiting from the fluid present in fluid system II, i.e. dialyzing fluid. Since dialyzing fluid lines 10, 11 are transparent hose lines, the light can be coupled by the hose line into the dialyzing fluid and can be decoupled from the dialyzing fluid. Measuring arrangement 21 is arranged on dialyzing fluid return line 11, in particular in the section of dialyzing fluid return line 11 downstream of dialyzing fluid chamber 4 of dialyzer 1 or filter and upstream of dialyzing fluid pump 13. The measurement can take place both at a measurement chamber intended for one-time use or at a permanently installed measurement chamber of the hose line. A cell can also be used as a measurement chamber. Apart from output-side light sensor 21B, the measuring arrangement can also comprise an input-side light sensor 21C, which measures the light emitted by light source 21A.

In the event of a rupture of semipermeable membrane 2 of dialyzer 1 or filter, blood from extracorporeal blood circuit I enters into dialyzing fluid chamber 4 of dialyzer 1 or filter both with the operation of the hemodiafiltration apparatus as a hemodialysis apparatus as well as a hemofiltration apparatus. The non-hemolysised blood can then be detected by measuring arrangement 21 in the dialyzing fluid which is flowing in dialyzing fluid system II. If the hemodiafiltration apparatus is being operated solely as a hemofiltration apparatus, the blood can be detected in the filtrate which is withdrawn from dialyzing fluid chamber 4. In the event of a hemolysis due to kinking of the arterial or venous blood line 5, 7 or a systemically caused hemolysis, hemoglobin or hemolysised blood gets through intact semipermeable membrane 2 of dialyzer 1 or filter into dialyzing fluid chamber 4, which can also be detected by measuring arrangement 21.

Located downstream of drip chamber 8 on venous blood line 7 is a shut-off element 18 for shutting off blood line 7. Shut-off element 18, in particular an electromagnetically actuated hose clamp, is connected via a control line 18' to control and computing unit 17.

The device for the detection of blood or blood constituents comprises an evaluation unit 20, which is connected via a data line 20' to central control and computing unit 17 of the hemodiafiltration apparatus. Evaluation unit 20, however, can also be a component of control and computing unit 17. The evaluation unit receives the signals of output-side light sensor 21B via a data line 21' and the signals of input-side light sensor 21C of measuring arrangement 21 via a data line 21". Evaluation unit 20 can comprise a control unit which, depending on the intensity of the light emitted by light source 21A that is measured by output-side light sensor 21B, controls the light source in such a way that the light intensity remains constant independently of the ambient conditions.

The result of the monitoring is signaled by a signal unit 22, which is connected via a data line 22' to evaluation unit 20. Signal unit 22 comprises a display screen 22A for displaying symbols or text and an alarm emitter 22B for generating an acoustic or tactile alarm. Patient-specific data can be inputted on input unit 23, which is connected via a data line 23' to evaluation unit 20. Input unit 23 can also be a touchscreen, which serves as a display screen of the signal unit.

Light source 21A of measuring arrangement 21 emits white light, which contains the color components red, green and blue with a specific intensity $I_0$. Light source 21A can be connected via a control line 21A' to central control and computing unit 17, so that intensity $I_0$ of the light can be preselected by control and computing unit 17. Light sensor 21B receives the light of light source 21A passing through the dialyzing fluid (filtrate). The light sensor is a sensor which can evaluate intensity $I_1$ of three color components red, green and blue (RGB). The light-sensitive surface of the sensor is formed by a large number of identical photodiodes, which are arranged in rows and columns. A color filter is assigned in each case to each photodiode. A red color filter is provided for the evaluation of the red component, a green color filter for the evaluation of the green component and a blue color filter for the evaluation of the blue component of the light.

Figure 2:
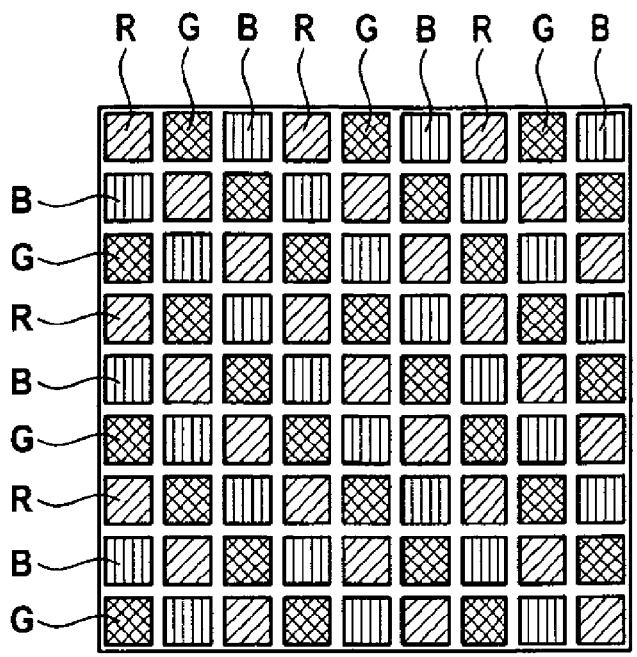
FIG. 2 shows a schematic representation of the measurement field of the light sensor of the device for the detection of blood or blood constituents.
Figure 3:
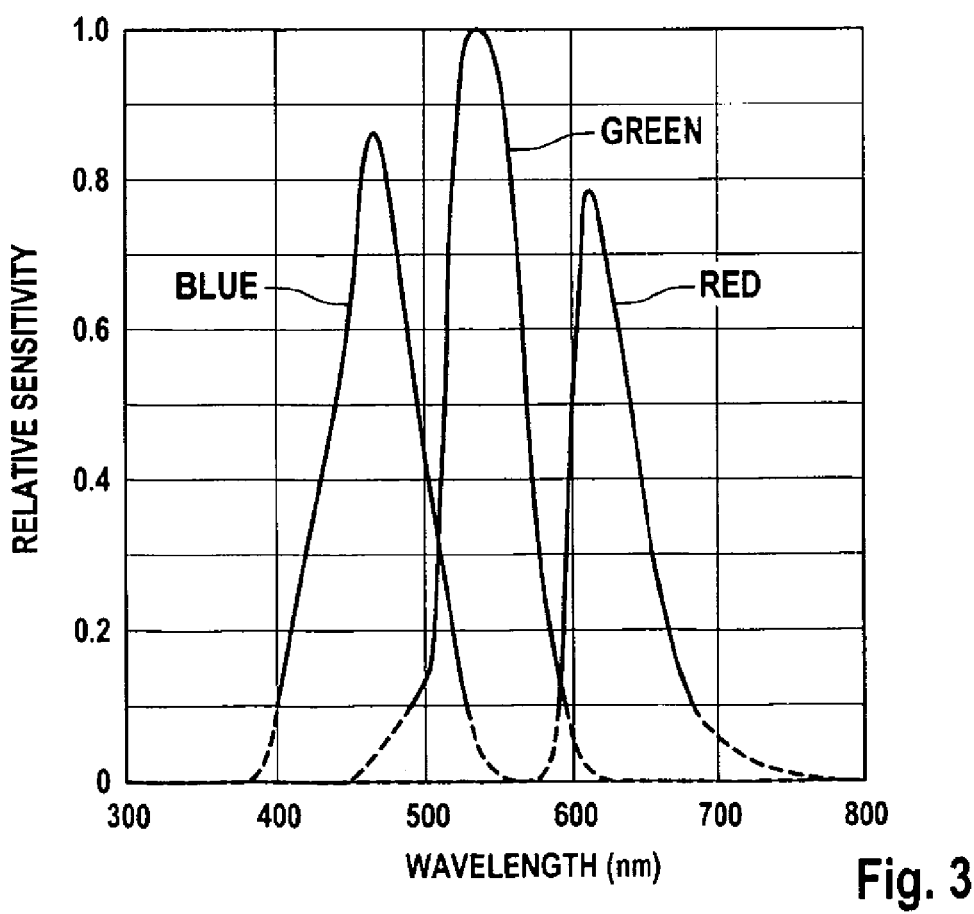
FIG. 3 shows a schematic representation of the relative sensitivity of the light sensor as a function of the wavelength of the light.

FIG. 2 shows the chessboard-like arrangement of the photodiodes with the color filters. The color filters are denoted by R (red), G (green) and B (blue). Light sensor 21B delivers an electrical output signal which contains information concerning the intensity of the red, green and blue component of the light. FIG. 3 shows, in a schematic representation, the relative sensitivity of the sensor for the individual color components blue, green and red. Since the light sensor forms an image not only of an individual measurement point, but a measurement field, sensor 21B delivers an output signal integrated over the light-sensitive surface.

The light sensor can for example be a sensor of the brand "Programmable Color Light-to-Frequency Converter TCS230" from the Firm TAOS (Texas Advanced Optoelectronic Solutions Inc., Plano, Tex., USA) or a sensor of the brand "Digital Color Sensor S9706" from the firm Hamamatsu (Hamamatsu Photonics K.K., Japan) or suchlike. The structure and function of the two sensors are described in detail in the manufacturers' data sheets.

The mode of functioning of the device according to the present invention for distinguishing between blood and hemoglobin in the dialyzing fluid (filtrate) is described below.

Evaluation unit 20 receives output signal S of output-side light sensor 21B of measuring arrangement 21, said output signal containing the three light components red, green and blue.

In evaluation unit 20, the output signal of the sensor is broken down into the three individual signals for the color components red, green and blue (RGB). The amount of the individual signals (signal strength) is proportional to intensity $I_1$ of the light exiting from the dialyzing fluid (filtrate). Intensity $I_0$ of the light entering into the dialyzing fluid (filtrate) is determined by light source 21A and is measured by input-side light sensor 21C. Evaluation unit 20 now determines quotient R/B from intensity $I_1$ of red component R of the light exiting from the fluid, i.e. the amount of the individual signal for the red component, and intensity $I_1$ of blue component B of the light exiting from the fluid, i.e. the amount of the individual signal for the blue component. Moreover, the evaluation unit can calculate quotient R/G from intensity $I_1$ of the red component and of the green component, i.e. the quotient of the individual signals of the red and green component. Furthermore, the evaluation unit calculates quotient G/B of intensity $I_1$ of the green component and the blue component. All the quotients are stored in an internal memory of the evaluation unit. The measurement can take place at preset time intervals or continuously. It is also possible to carry out reference measurements at specific times, for example before the treatment, in order to be able to compare the current values with the reference values. The reference measurements can also take place cyclically, for example using a bypass which bypasses the dialyzer or filter.

The bypass for bypassing the dialyzer for the reference measurements comprises a bypass line 24, which departs from dialyzing fluid supply line 10 upstream of dialyzing fluid chamber 4 and leads to dialyzing fluid discharge line 11 downstream of the dialyzing fluid chamber. A shut-off element 25 for opening and closing the bypass line is located in bypass line 24 and a shut-off element 26 for cutting off the dialyzing fluid chamber is located in the section of dialyzing fluid supply line 10 between bypass line 24 and dialyzing fluid chamber 4. The two shut-off elements 25, 26 are connected via control lines 25', 26' to central control and computing unit 17. In order to bypass dialyzer 1, the control unit opens shut-off element 25 and closes shut-off element 26. Otherwise, shut-off element 25 is closed and shut-off element 26 is open.

Figure 4:
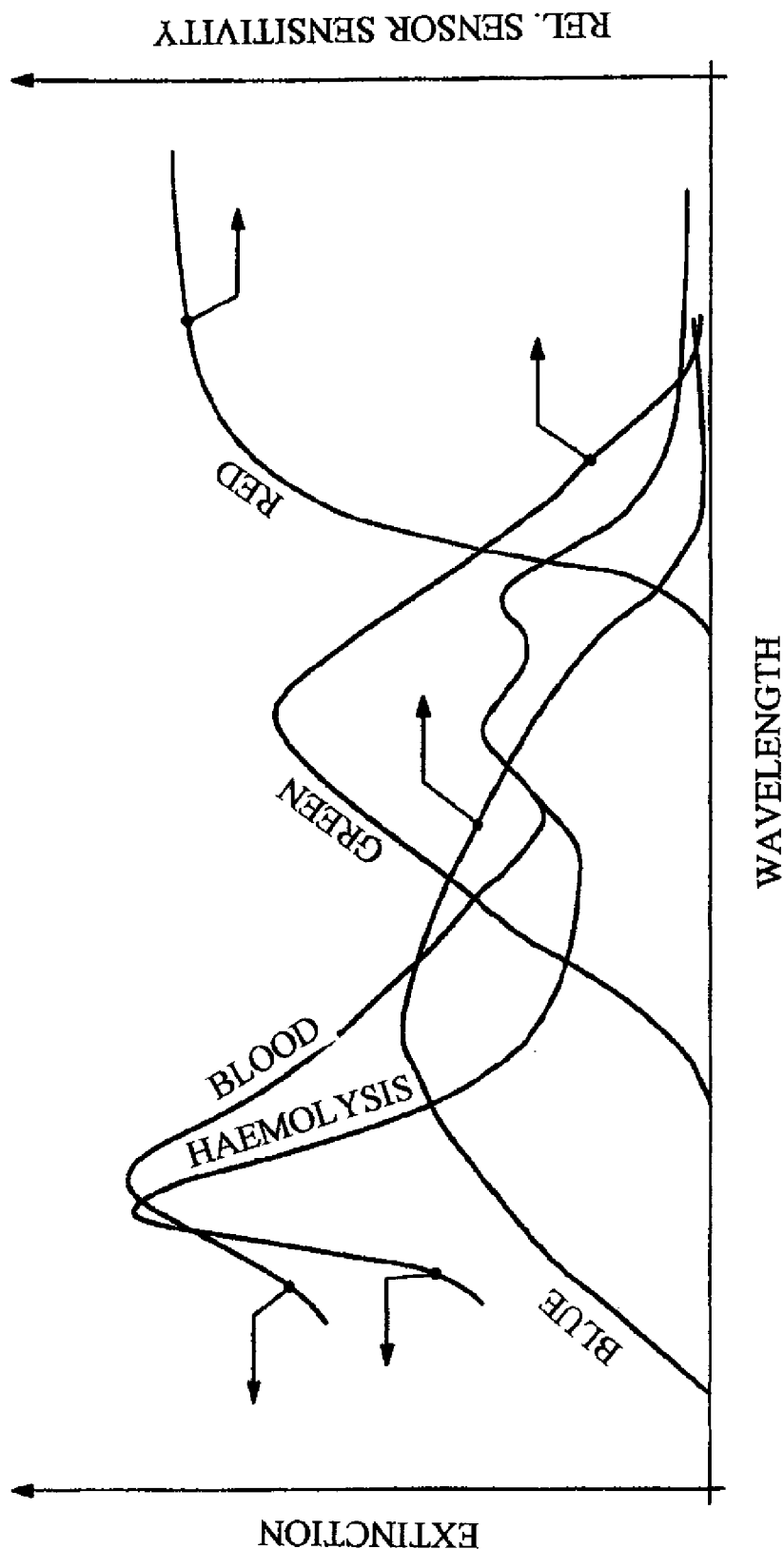
FIG. 4 shows a schematic representation of the extinction as a function of the wavelength for the case of the entry of blood or of hemoglobin into the dialyzing fluid.

FIG. 4 shows schematically the characteristic courses of the extinction for intact blood in the dialysate on the one hand and for hemolysised blood in the dialysate on the other hand as well as the relative sensitivity of the sensor as a function of the wavelength. It can be seen that considerable differences for intact blood and hemolysised blood are present in the region of blue to green light, because the hemolysised blood brings free hemoglobin into the dialysate. In the region of green to red light, on the other hand, scarcely any differences can be detected. The graph of the extinction for intact blood in the dialysate differs, amongst other things, in the region of the blue spectrum from the graph of the extinction for the hemolysised blood in the dialysate.

Figure 5:
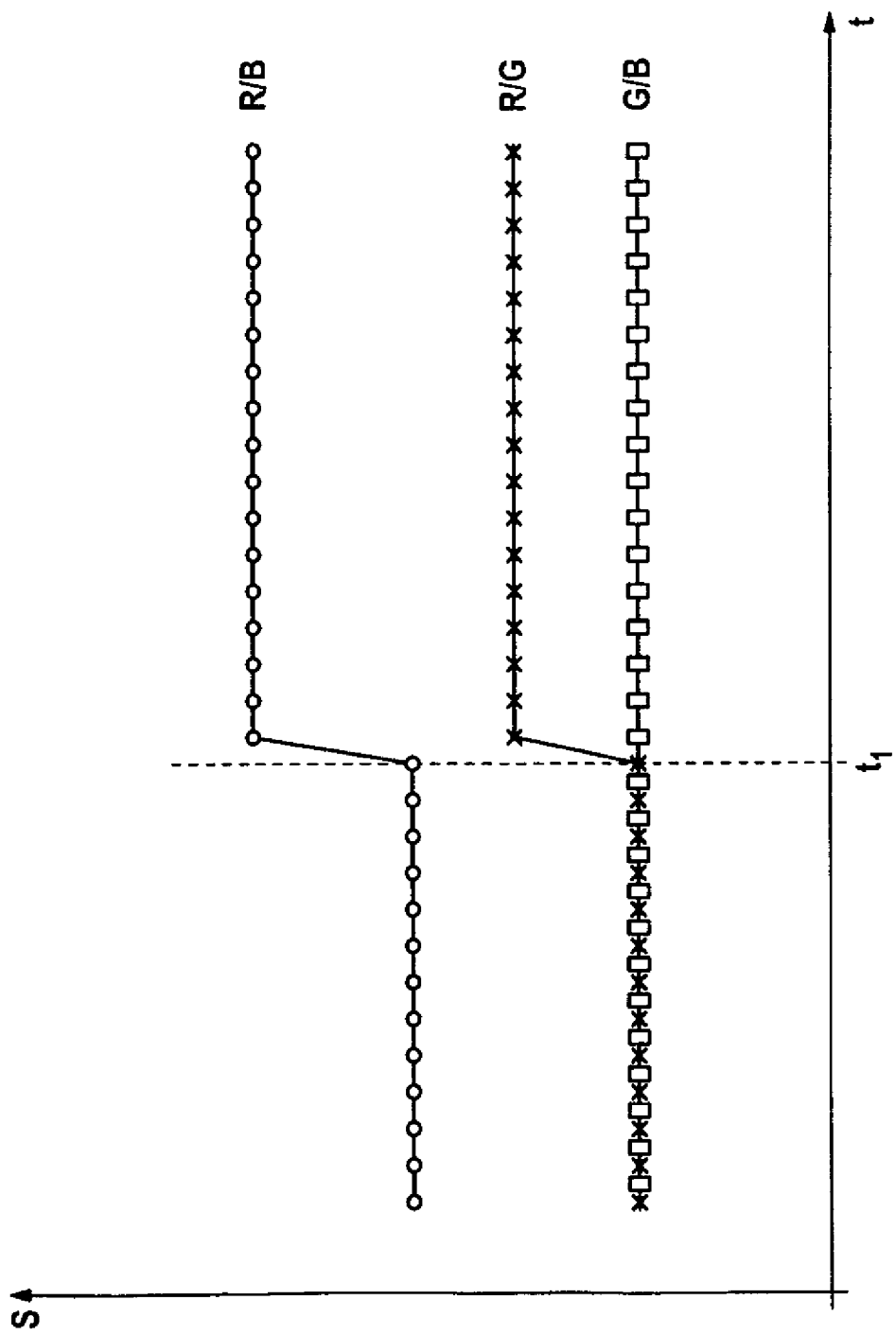
FIG. 5 shows the change in the signal strength of the light sensor for the individual color components of light before and after the entry of hemoglobin into the dialyzing fluid.

FIG. 5 shows the amount of the quotient of individual signals S of the color sensor for the individual color components of the light RED/BLUE (R/B), RED/GREEN (R/G), GREEN/BLUE (G/B) as a function of time before the entry ($t<t_1$) and after the entry ($t>t_1$) of the hemolysised blood into the dialysate. It can be seen that the amount of the quotient of the red and blue component (RED/BLUE) and the amount of the quotient of the red and green component (RED/GREEN) increases significantly with the addition of hemoglobin, whereas the amount of the quotient of the green and blue component (GREEN/BLUE) scarcely changes or does so insignificantly.

Figure 6:
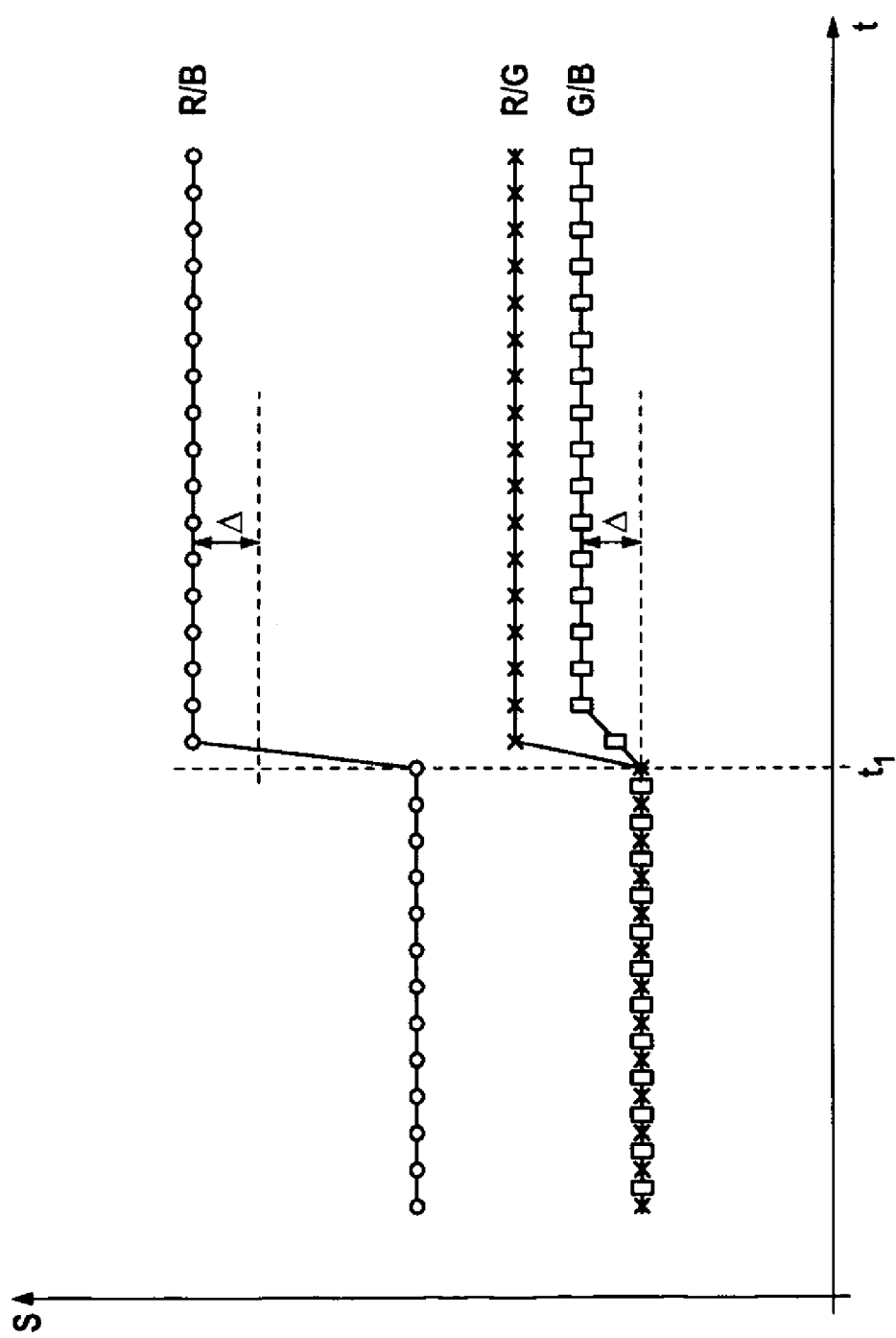
FIG. 6 shows the change in the signal strength of the light sensor for the individual color components before and after the entry of blood into the dialyzing fluid.

FIG. 6 shows the case of the entry of non-hemolysised blood into the dialysate. It can be seen that the amount of all the quotients (RED/BLUE, RED/GREEN and GREEN/BLUE) increases significantly with the entry of non-hemolysised blood. A comparison of FIGS. 5 and 6 shows that the entry of non-hemolysised blood (FIG. 6) leads however to a more marked increase in the amount of the quotient of the red and blue component (RED/BLUE) than the entry of hemolysised blood (FIG. 5). Whereas the amount of the quotient of the green and blue component (GREEN/BLUE) remains virtually unchanged with the entry of hemolysised blood (FIG. 5), the amount of the quotient of the green and blue component (GREEN/BLUE) increases with the entry of non-hemolysised blood. On the other hand, no significant difference can be seen in FIGS. 5 and 6 in the amount of the quotient of the red and green component (RED/GREEN).

The difference in the increase of the amount of the quotient of the red and blue component (RED/BLUE) with hemolysised blood and non-hemolysised blood and the difference between the amount of the quotient of the green and blue component (GREEN/BLUE) with hemolysised and non-hemolysised blood is denoted by A in FIG. 6.

In a first embodiment, evaluation unit 20 compares the quotient of the red and blue component (RED/BLUE) with a preset threshold value, which can be changed depending on the method. In this embodiment, only the quotient R/B of the red and blue component needs to be calculated, which is compared with the preset threshold value. If the quotient of the red and blue component (RED/BLUE) lies above the preset threshold value, evaluation unit 20 concludes that there is an entry of non-hemolysised blood, for example due to a membrane rupture (FIG. 6), whereas the evaluation unit concludes that there is an entry of hemolysised blood, for example as a result of blood damage due for example to a kinked hose line or a systemically related hemolysis (FIG. 5), if the quotient of the red and blue component (RED/BLUE) is less than or equal to the preset threshold value.

In an alternative embodiment, evaluation unit 20 does not calculate the quotient of the red and blue component, but rather the quotient of the green and blue component. The evaluation unit concludes that there is an entry of non-hemolysised blood (FIG. 6) if the quotient of the green and blue component (GREEN/BLUE) is greater than the preset threshold value, whereas the evaluation unit concludes that there is an entry of hemolysised blood (FIG. 5) if the quotient of the green and blue component is equal to or less than the preset threshold value.

It is also possible for both quotients (RED/BLUE) and (GREEN/BLUE) to be determined and evaluated statistically.

For example, it is possible for the evaluation unit to conclude that there is only an entry of non-hemolysised blood if both the quotient of the red and blue component and the quotient of the green and blue component lie above the preset threshold values.

In principle, however, it is also possible to evaluate solely the blue component of the light, which is related neither to the red component nor to the green component.

In a preferred embodiment, evaluation unit 20 determines not only the quotient of the red and blue component and/or the green and blue component in order to be able to distinguish between the entry of a hemolysised and non-hemolysised blood, but also the quotient of the red and green component which is stored in the memory. The quotient of the red and green component (RED/GREEN) is compared in evaluation unit 20 with a first preset threshold value. If the quotient of the red and green component (RED/GREEN) is greater than the preset first threshold value, the evaluation unit concludes that there is an entry of hemolysised blood or non-hemolysised blood into the dialyzing fluid. Otherwise, it is not concluded that there is an abnormal occurrence. Only if the evaluation unit has ascertained an abnormal occurrence, i.e. the quotient of the red and green component (RED/GREEN) is greater than the preset first threshold value, does the evaluation unit initiate the steps described above in order to be able to distinguish between the entry of hemolysised blood or non-hemolysised blood. The evaluation unit then calculates the quotient of the red and blue component (RED/BLUE), which is compared with a preset second threshold value, and/or the quotient of the green and blue component (GREEN/BLUE), which is compared with a preset third threshold value, as described above.

The present threshold values can be stored in a memory in evaluation unit 20. The preset threshold values are therefore permanently preselected. In an alternative embodiment, the preset threshold values are adapted to the patient. For this purpose, evaluation unit 20 comprises means for adapting the threshold value to patient-specific data, which are inputted on input unit 23. For example, it is possible to preselect, for patients suffering from a systemic hemolysis, a higher threshold value than for patients in which hemoglobin in the blood is not raised. After the inputting of the patient-specific data for a patient suffering from a systemic hemolysis, the evaluation unit therefore carries out a correction to the otherwise preselected threshold value with a specific correction factor.

An alternative embodiment provides for the determination of the threshold value with a reference measurement, which is carried out before or at the start of or during the blood treatment at a time at which it is assumed that there is no complication. This reference measurement is used to ascertain hemoglobin values possibly raised due to a systemic hemolysis, from which a corresponding correction factor is calculated.

If the evaluation unit detects the entry of hemolysised blood due for example to kinking of a hose line or the entry of non-hemolysised blood due for example to a membrane rupture, the result of the verification is signaled by means of signal unit 22. For example, an acoustic and/or optical and/or tactile alarm is emitted by alarm emitter 22B. Optical alarm signals can be displayed on display screen 22A of signal unit 22. A prompt for a targeted countermeasure can also be shown on the display screen. For example, it can be shown on the display screen that the hose system or the dialyzer needs to be replaced. It is also possible to indicate on the display screen that, although hemoglobin is detected in the dialysate, it cannot be traced back to a hemolysis as a result of damage to the blood in the extracorporeal circuit, but rather to a systemically related hemolysis of the patient.

Apart from the signaling of complications in the extracorporeal blood treatment, it is also possible for the evaluation unit to generate a control signal for intervention in the machine control, which is received by central control and computing unit 17 of the extracorporeal blood treatment apparatus. In the event that the evaluation unit detects a membrane rupture, the evaluation unit generates a control signal for the immediate interruption of the blood treatment. Central control and computing unit 17 then immediately interrupts the blood delivery by closing hose clamp 18 and stopping blood pump 6. A prompt now appears on the display screen to replace dialyzer 1 or the filter, while an acoustic alarm is emitted with alarm emitter 22B.

What is claimed is:

1. A device for the detection of blood or blood constituents in a fluid system of an extracorporeal blood treatment apparatus, said extracorporeal blood treatment apparatus comprising a dialyzer or filter divided by a semipermeable membrane into a first chamber and a second chamber, wherein the first chamber is part of an extracorporeal blood circuit and the second chamber is part of the fluid system, said device comprising:
   a light source for emitting light that enters into a fluid present in the fluid system;
   a light sensor for receiving light that exits from the fluid present in the fluid system; and
   an evaluation unit configured to:
   evaluate an intensity $I_1$ of the light exiting from the fluid; and
   distinguish between an entry of blood into the fluid system due to a defect in the dialyzer or filter, and an entry of hemoglobin into the fluid system due to a hemolysis, on the basis of the change in the intensity $I_1$ of the light exiting from the fluid.

2. The device according to claim 1, wherein the evaluation unit is further configured to:
   distinguish between the entry of blood into the fluid due to a defect in the dialyzer or filter, and the entry of hemoglobin into the fluid system due to a hemolysis, at least on the basis of the change in the intensity $I_1$ of a blue component of the light exiting from the fluid.

3. The device according to claim 1, wherein the light source is configured to emit light that comprises at least a blue component and a red component, and
   wherein the light sensor is configured to receive light that comprises at least a blue component and a red component, and
   wherein the evaluation unit is further configured to:
   determine an intensity $I_{1/B}$ of the blue component of the light exiting from the fluid;
   determine an intensity $I_{1/R}$ of the red component of the light exiting from the fluid;
   compare the intensity $I_{1/R}$ of the red component with the intensity $I_{1/B}$ of the blue component; and
   distinguish between the entry of blood into the fluid system and a hemolysis on the basis of the comparison between the intensity $I_{1/R}$ of the red component and the intensity $I_{1/B}$ of the blue component.

4. The device according to claim 3, wherein the evaluation unit is further configured to:
   calculate the quotient (R/B) of the intensity of red component R and the intensity of blue component B;
   compare the quotient (R/B) with a preset threshold value; and
   determine that there is an entry of blood if the quotient (R/B) is greater than the preset threshold value, or determine that there is a hemolysis if the quotient (R/B) is less than or equal to the preset threshold value.

5. The device according to claim 1, wherein the light source is configured to emit light that comprises a blue component and a green component, and
   wherein the light sensor is configured to receive light that comprises a blue component and a green component, and
   wherein the evaluation unit is further configured to:
   determine an intensity $I_{1/B}$ of the blue component of the light exiting from the fluid;
   determine an intensity $I_{1/G}$ of the green component of the light exiting from the fluid;
   compare the intensity $I_{1/G}$ of green component with the intensity $I_{1/B}$ of blue component; and
   distinguish between the entry of blood into the fluid system and a hemolysis on the basis of the comparison between the intensity $I_{1/G}$ of the green component and the intensity $I_{1/B}$ of the blue component.

6. The device according to claim 5, wherein the evaluation unit is further configured to:
   calculate the quotient (G/B) of the intensity of the green component G and the intensity of the blue component B;
   compare the quotient (G/B) with a preset threshold value; and
   determine that there is an entry of blood if the quotient (G/B) is greater than the preset threshold value, or determine that there is a hemolysis if the quotient (G/B) is less than or equal to the threshold value.

7. The device according to claim 1, wherein the light source is configured to emit light that comprises a red component, a green component, and a blue component, and
   wherein the light sensor is configured to receive light that comprises a red component, a green component and a blue component, and
   wherein the evaluation unit is further configured to:
   determine an intensity $I_{1/R}$ of the red component of the light exiting from the fluid;
   determine an intensity $I_{1/G}$ of the green component of the light exiting from the fluid;
   determine an intensity $I_{1/B}$ of the blue component of the light exiting from the fluid;
   compare the intensity $I_{1/R}$ of the red component with the intensity $I_{1/G}$ of green component in a first step; and determine that there is an entry of blood into the fluid system or a hemolysis on the basis of the comparison between the intensity $I_{1/G}$ of the green component and the intensity $I_{1/R}$ of the red component; and
   if there is an entry of blood or a hemolysis found in the first step, then compare the intensity $I_{1/R}$ of the red component with the intensity $I_{1/B}$ of the blue component in a second step, and distinguish between the entry of blood into the fluid system and a hemolysis on the basis of the comparison between the intensity $I_{1/R}$ of the red component and the intensity $I_{1/B}$ of the blue component.

8. The device according to claim 7, wherein the evaluation unit is further configured to:
   calculate the quotient (R/G) of the intensity of the red component R and the intensity of green component G in the first step;
   determine that there is an entry of blood or a hemolysis if the quotient (R/G) is greater than a preset first threshold value;

calculate the quotient (R/B) of the intensity of red component R and the intensity of blue component B in the second step; and determine that there is an entry of blood if the quotient (R/B) is greater than a preset second threshold value or that there is a hemolysis if the quotient (R/B) is less than or equal to the preset second threshold value.

9. The device according to claim 1, wherein the light source is configured to emit light that comprises a red component, a green component, and a blue component, and wherein the light sensor is configured to receive light that comprises a red component, a green component and a blue component, and wherein the evaluation unit is configured to:

determine the intensity $I_{1/R}$ of the red component of the light exiting from the fluid;

determine the intensity $I_{1/G}$ of the green component of the light exiting from the fluid;

determine the intensity $I_{1/B}$ of the blue component of the light exiting from the fluid;

compare the intensity $I_{1/R}$ of the red component with the intensity $I_{1/G}$ of green component in a first step;

determine that there is an entry of blood into the fluid system or a hemolysis on the basis of the comparison between the intensity $I_{1/G}$ of the green component and the intensity $I_{1/R}$ of the red component; and if there is an entry of blood or a hemolysis found in the first step, then compare the intensity $I_{1/G}$ of the green component with the intensity $I_{1/B}$ of the blue component in a second step; and distinguish between the entry of blood into the fluid system and a hemolysis on the basis of the comparison between the intensity $I_{1/G}$ of the green component and the intensity $I_{1/B}$ of the blue component;

calculate the quotient (R/G) of the intensity of red component R and the intensity of green component G in the first step, and determine that there is an entry of blood or a hemolysis if the quotient (R/G) is greater than a preset first threshold value; and calculate the quotient (G/B) of the intensity of green component G and the intensity of blue component B in the second step; and determine that there is an entry of blood if the quotient (G/B) is greater than a preset second threshold value or that there is a hemolysis if the quotient (G/B) is less than or equal to the preset second threshold value.

10. The device according to claim 1, further comprising:

a second light sensor for receiving light that enters into the fluid present in the fluid system, wherein the evaluation unit is further configured to:

compare the intensity $I_0$ of the light entering into the fluid with a preset threshold value.

11. The device according to claim 1, wherein the light source is configured to emit white light, and the light sensor is configured to receive different color components of light.

12. A device for extracorporeal blood treatment comprising:

a dialyzer or filter divided by a semipermeable membrane into a first chamber and a second chamber, wherein the first chamber is part of the extracorporeal blood circuit and the second chamber is part of a fluid system; and a device for the detection of blood or blood constituents in the fluid system comprising:

a light source for emitting light that enters into a fluid present in the fluid system;

a light sensor for receiving light that exits from the fluid present in the fluid system; and an evaluation unit configured to:

evaluate the intensity $I_1$ of the light exiting from the fluid; and distinguish between an entry of blood into the fluid system due to a defect in the dialyzer or filter, and an entry of hemoglobin into the fluid system due to a hemolysis, on the basis of the change in the intensity $I_1$ of the light exiting from the fluid.

13. A method for the detection of blood or blood constituents in the fluid system of an apparatus for extracorporeal blood treatment, said extracorporeal blood treatment apparatus comprising a dialyzer or filter divided by a semipermeable membrane into a first chamber and a second chamber, wherein the first chamber is part of an extracorporeal blood circuit and the second chamber is part of the fluid system, said method comprising:

emitting light that enters into the fluid present in the fluid system;

receiving light that exits from the fluid present in the fluid system;

evaluating an intensity $I_1$ of the light exiting from the fluid; and distinguishing between an entry of blood into the fluid system due to a defect in the dialyzer or filter, and an entry of hemoglobin into the fluid system due to a hemolysis, on the basis of the change in the intensity $I_1$ of the light exiting from the fluid.

14. The method according to claim 13, further comprising:

distinguishing between the entry of blood into the fluid system due to a defect in the dialyzer or filter, and the entry of hemoglobin into the fluid system due to a hemolysis, at least on the basis of the change in the intensity $I_1$ of a blue component of the light exiting from the fluid.

15. The method according to claim 13, further comprising:

emitting light that comprises at least a blue component and a red component;

receiving light that comprises at least a blue component and a red component; and determining an intensity $I_{1/B}$ of the blue component of the light exiting from the fluid;

determining an intensity $I_{1/R}$ of the red component of the light exiting from the fluid;

comparing the intensity $I_{1/R}$ of the red component with the intensity $I_{1/B}$ of the blue component; and distinguishing between the entry of blood into the fluid system and a hemolysis on the basis of the comparison between the intensity $I_{1/R}$ of red component and the intensity $I_{1/B}$ of blue component.

16. The method according to claim 15, further comprising:

calculating the quotient (R/B) of the intensity of the red component R and the intensity of the blue component B;

comparing the quotient (R/B) with a preset threshold value; and determining that there is an entry of blood if the quotient (R/B) is greater than the preset threshold value or determining that there is a hemolysis if the quotient (R/B) is less than or equal to the preset threshold value.

17. The method according to claim 13, further comprising:

emitting light that comprises at least a blue component and a green component;

receiving light that comprises at least a blue component and a green component;

determining an intensity $I_{1/B}$ of the blue component of the light exiting from the fluid;

determining an intensity $I_{1/G}$ of the green component of the light exiting from the fluid;

comparing the intensity $I_{1/G}$ of green component with the intensity $I_{1/B}$ of blue component; and distinguishing between the entry of blood into the fluid system and a hemolysis on the basis of the comparison of the intensity $I_{1/G}$ of the green component and the intensity $I_{1/B}$ of blue component by:

calculating the quotient (G/B) of the intensity of green component G and the intensity of blue component B;

comparing the quotient (G/B) with a preset threshold value; and determining that there is an entry of blood if the quotient (G/B) is greater than the preset threshold value, or determining that there is a hemolysis if the quotient (G/B) is less than or equal to the preset threshold value.

18. The method according to claim 13, further comprising:

emitting light that comprises a red component, a green component and a blue component;

receiving light comprises a red component, a green component and a blue component;

determining an intensity $I_{1/R}$ of the red component of the light exiting from the fluid;

determining an intensity $I_{1/G}$ of the green component of the light exiting from the fluid;

determining an intensity $I_{1/B}$ of the blue component of the light exiting from the fluid;

comparing the intensity $I_{1/R}$ of the red component with the intensity $I_{1/G}$ of green component in a first step; and determining that there is an entry of blood into the fluid system or a hemolysis on the basis of the comparison between the intensity $I_{1/R}$ of the red component and the intensity $I_{1/G}$ of the green component; and if there is an entry of blood or a hemolysis found in the first step, then comparing the intensity $I_{1/R}$ of the red component with the intensity $I_{1/B}$ of the blue component in a second step, and distinguishing between the entry of blood into the fluid system and a hemolysis on the basis of the comparison between the intensity $I_{1/R}$ of the red component and the intensity $I_{1/B}$ of the blue component by:

calculating the quotient (R/G) of the intensity of the red component R and the intensity of green component G in the first step;

determining that there is an entry of blood or a hemolysis if the quotient (R/G) is greater than a preset first threshold value;

calculating the quotient (R/B) of the intensity of the red component R and the intensity of blue component B in the second step; and determining that there is an entry of blood if the quotient (R/B) is greater than a preset second threshold value or that there is a hemolysis if the quotient (R/B) is less than or equal to the preset second threshold value.

19. The method according to claim 13, further comprising:

emitting light that comprises a red component, a green component and a blue component;

receiving light that comprises a red component, a green component and a blue component;

determining an intensity $I_{1/R}$ of the red component of the light exiting from the fluid;

determining an intensity $I_{1/G}$ of the green component of the light exiting from the fluid;

determining an intensity $I_{1/B}$ of the blue component of the light exiting from the fluid;

comparing the intensity $I_{1/R}$ of the red component with the intensity $I_{1/G}$ of green component in a first step, determining that there is an entry of blood into the fluid system or a hemolysis on the basis of the comparison between the intensity $I_{1/R}$ of the red component and the intensity $I_{1/G}$ of the green component;

if there is an entry of blood or a hemolysis found in the first step, then comparing the intensity $I_{1/G}$ of the green component with the intensity $I_{1/B}$ of the blue component in a second step, and distinguishing between the entry of blood into the fluid system and a hemolysis on the basis of the comparison between the intensity $I_{1/G}$ of the green component and the intensity $I_{1/B}$ of the blue component by:

calculating the quotient (R/G) of the intensity of the red component R and the intensity of green component G in the first step; and determining that there is an entry of blood or a hemolysis if the quotient (R/G) is greater than a preset first threshold value; and calculating the quotient (G/B) of the intensity of the green component G and the intensity of blue component B in the second step; and determining that there is an entry of blood if the quotient (G/B) is greater than a preset second threshold value or determining that there is a hemolysis if the quotient (G/B) is less than or equal to the preset second threshold value.

20. The device according to claim 13, further comprising:

receiving light that enters into the fluid present in the fluid system; and comparing an intensity $I_0$ of the light entering into the fluid with a preset threshold value.

* * * * *